United States Patent [19]

Ishida et al.

[11] Patent Number: 4,514,635
[45] Date of Patent: Apr. 30, 1985

[54] NON-DISPERSIVE INFRARED ANALYZER

[75] Inventors: Kozo Ishida; Takao Imaki, both of Kyoto, Japan

[73] Assignee: Horiba, Ltd., Kyoto, Japan

[21] Appl. No.: 437,885

[22] Filed: Oct. 29, 1982

[30] Foreign Application Priority Data

Nov. 26, 1981 [JP] Japan .................................. 56-191331

[51] Int. Cl.³ .............................................. G01J 1/00
[52] U.S. Cl. ...................................... 250/343; 250/344
[58] Field of Search ............... 250/339, 341, 343, 344, 250/345

[56] References Cited

U.S. PATENT DOCUMENTS 4,320,297  3/1982  Cederstrand et al. ............... 250/343
4,336,453  6/1982  Imaki et al. ......................... 250/344
4,393,304  7/1983  Ishida et al. ........................ 250/343

Primary Examiner—Janice A. Howell
Attorney, Agent, or Firm—Wenderoth, Lind & Ponack

[57] ABSTRACT

A non-dispersive infrared analyzer for determining the concentration of two components of a sample fluid. A zero fluid and a sample fluid are alternately supplied to two cells. Two pneumatic detectors are respectively optically arranged in series with two light sources such that the two cells are respectively sandwiched between the two light sources and the two detectors. At least one filter whose passband corresponds to the absorbtion bands of one of the two components of the sample fluid is located directly adjacent to and optically in series with at least one of the two cells.

8 Claims, 5 Drawing Figures

NON-DISPERSIVE INFRARED ANALYZER

BACKGROUND OF THE INVENTION

1. Field of the Invention

The present invention relates to a non-dispersive type infrared analyzer which can simultaneously determine the concentration of two kinds of components contained within a fluid sample.

2. Description of the Prior Art

A prior art analyzer is shown in FIG. 1. Such an analyzer adopts a "cross modulation system" in which the zero fluid and the sample fluid are alternately provided in two cells 2 and 2' by changing over a passage-changing over member 6 at a definite period. In addition, a pneumatic detector 7 having light-receiving chambers 7a and 7b and a pneumatic detector 8 having light-receiving chambers 8a and 8b are arranged in series with respect to light-passages through which light generated by light sources 1 and 1' pass through cells 2 and 2'; an analyzer of this type has an advantage in that it is relatively immune to changes in the ambient temperature and thermal fluctuations due to the use of a pneumatic detector having two light-receiving chambers in addition to such advantages as the absence of zero-drift and a good S/N ratio. However, such prior art analyzers also have disadvantages in that they are influenced by the mutual interference of the two components whose concentration is to be determined and by the interference of the other components contained within the sample fluid. In particular, in the case when the concentration of one of the components to be determined is lower than that of another component, there is the possibility that the error due to the interference in the determination of the concentration of the low-concentration gas is particularly large. Furthermore, in the high concentration-low concentration case described above, an analyzer as shown in FIG. 1 is not suitable for accurately determining the concentration of both components since it uses cells 2 and 2' having the same length.

That is the absorption in the cell, in which the sample fluid is provided, is changed in dependence upon the product of the concentration multiplied by the cell-length along a curve similar to that of Lambert-Beer's law, as shown in FIG. 2. The smaller the value of the absorption is, the better the linearity is. Consequently, the selection of the optimum cell-length for the low-concentration component whose concentration is to be determined leads to a curvature of the calibration curve and a wrong scale accuracy of the instrument when used in the determination of the concentration of another high-concentration component. Thus, a high linearity for the determination of the concentration of the high-concentration component which is attained by decreasing the cell-length leads to a low S/N ratio in the determination of the concentration of the low-concentration component.

SUMMARY OF THE INVENTION

It is an object of the present invention to eliminate the above described disadvantages by using an optical filter, which isolates portions of the IR spectrum so as to enhance the specificity of the measurement, and is arranged directly before or after at least one of the cells.

In addition, the length of each cell is selected so that it may be suitable for the concentration range to be determined for each component and a filter is inserted directly before or after at least one cell having the greater length.

DESCRIPTION OF THE PREFERRED EMBODIMENTS

Figure 1:
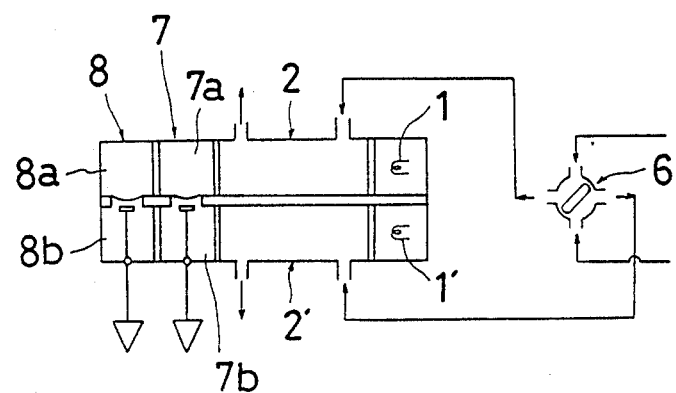
FIG. 1 is a block diagram showing a conventional non-dispersive infrared analyzer for determining the concentration of two components.
Figure 2:
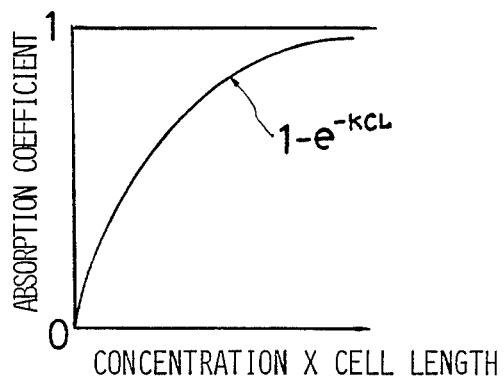
FIG. 2 is a graph showing the relationship between absorption coefficients and the products of the concentration multiplied by the cell length.
Figure 3:
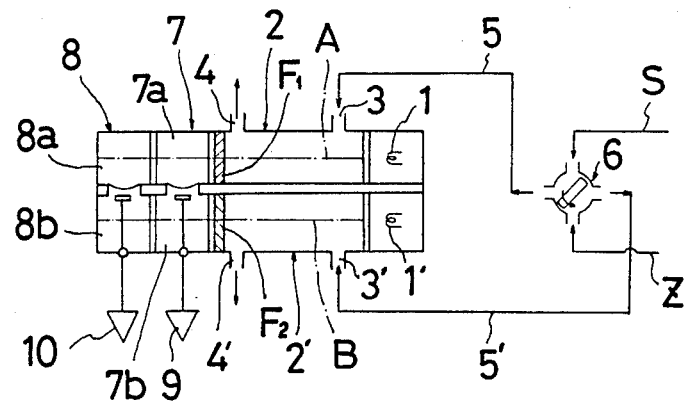
FIG. 3 is a block diagram showing one of the preferred embodiments of a non-dispersive infrared analyzer for determining the concentration of two components according to the present invention.
Figure 4:
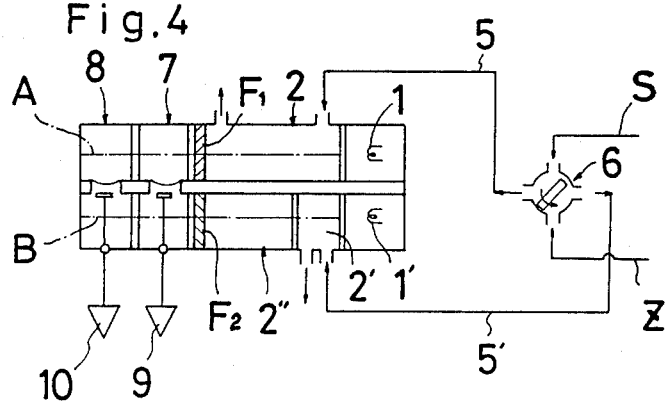
FIGS. 4 and 5 are block diagrams showing other preferred embodiments of non-dispersive infrared analyzers for determining the concentration of two components according to the present invention.
Figure 5:
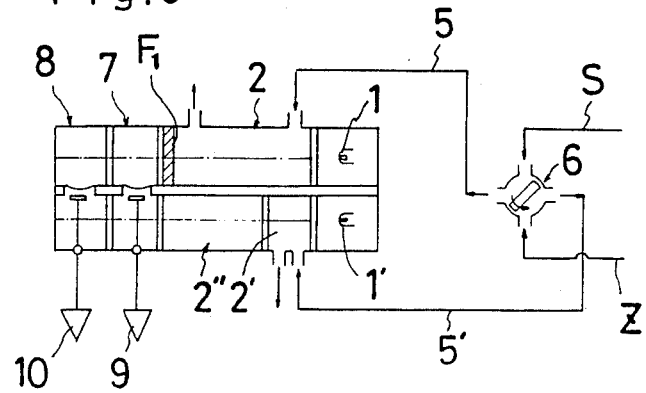

The present invention will be described in detail below by referring to the preferred embodiments as shown in FIGS. 3, 4, and 5.

Referring now to FIG. 3, which shows a non-dispersive infrared analyzer for determining the concentration of two components according to the present invention, elements 1 and 1' designate light sources for irradiating infrared rays; elements 2 and 2' designate two cells of equal length and respectively provided with inlets 3 and 3' and outlets 4 and 4'; fluid supply passages 5 and 5' are respectively connected to inlets 3 and 3' and are provided with a passage switch member 6 composed of a rotary valve and the like; a zero fluid (for example, a zero gas such as $N_2$) Z and a sample fluid (for example, a sample gas such as air, a combustion exhaust gas and the like) S are alternately supplied into the cells 2 and 2' by periodically switching over said passage switch member 6. Elements 7 and 8 are pneumatic detectors, for example, condenser microphone detectors, for detecting one of the two components whose concentration is to be determined; the pneumatic detectors 7 and 8 are arranged optically in series with the respective light sources 1 and 1'. That is, detectors 7 and 8 are respectively provided with two light-receiving chambers 7a and 7b, and 8a and 8b containing gaseous mixtures consisting of a component whose concentration is to be determined (or the components having the same absorption band as a component whose concentration is to be determined) and the zero gas at a definite partial pressures; the two light-receiving chambers 7a and 7b, and 8a and 8b are of the same size and shape, and the light-receiving chambers 7a and 7b, and 8a and 8b are respectively arranged in two optical paths A, B passing through the cells 2 and 2'. The gaseous mixtures to be enclosed in the light-receiving chambers are dependent upon the components whose concentrations are to be determined, for example, the gaseous mixture consisting of CO and the zero gas is enclosed in light-receiving chambers 7a and 7b while the gaseous mixture consisting of $CO_2$ and the zero gas is enclosed in light-receiving chambers 8a and 8b when the detector 7 is used for determining the concentration of CO and the detector 8 is used for determining the concentration of $CO_2$. In addition, it goes without saying that "a micro flow sensor", which uses the principle that the flow of gas due to a pressure differential generated by the absorption of infrared rays by gases enclosed in two light-receiving chambers acts upon a heated wire of, for example, platinum, extended between the two light-receiving chambers, can be used instead of a condenser microphone type detector. Elements 9 and 10 designate amplifiers.

A positive filter, whose passband corresponds to the absorption wavelength of one of the two components whose concentration is to be determined, such as an optical bandpass filter $F_1$ which is permeable only to infrared rays having frequencies corresponding to the absorption bands of CO, is inserted directly after (or before) one cell 2 of the pair of cells 2 and 2' and a positive filter, whose passband corresponds to the absorption wavelengths of the other of the two components whose concentration is to be determined, such as an optical bandpass filter $F_2$ which is permeable only to infrared rays having frequencies corresponding to the absorption bands of $CO_2$, is inserted directly after (or before) the other cell 2'.

According to the above described construction, the zero gas and the sample gas are alternately supplied to the cells 2 and 2' at a definite period by switching over the passage switch member 6. Infrared rays respectively irradiated by the light sources 1 and 1' through cells 2 and 2' are absorbed by the components in the sample gas whose concentration is to be determined (for example, CO and $CO_2$) during the time when the sample gas is supplied to the cells and pass through the same cells without being absorbed during the time when the zero gas is supplied to the cells. Infrared rays having wavelengths corresponding to absorption bands of one of the two components whose concentration is to be determined (for example, CO) are only incident upon chambers 7a and 8a arranged in the optical path A and only infrared rays having wavelengths corresponding to absorption bands of the other component (for example, $CO_2$) are incident upon the chambers 7b and 8b arranged in the optical path B since the positive filter $F_1$, whose passband corresponds to infrared rays having absorption bands of one of the two components whose concentration is to be determined (for example, CO), is inserted in the optical path A passing through one cell 2 and the positive filter $F_2$, whose passband corresponds to infrared rays having absorption bands of the other component (for example, $CO_2$), is inserted in the optical path B passing through the other cell 2'. Consequently, only infrared rays passing through the optical path A, i.e.—infrared rays having absorption bands of one of the two components whose concentration is to be determined (for example, CO) and either containing the concentration information or not containing the concentration information are alternately incident upon the detector 7 and only infrared rays passing through the optical path B, i.e.—infrared rays having absorption bands of another component (for example, $CO_2$) and either containing the concentration information or not contains the concentration information are alternately incident upon the detector 8; thus, the influences of the mutual interference caused by the components in the sample gas other than those components whose concentration is to be determined can be prevented and the S/N ratio can be improved.

FIG. 4 shows another preferred embodiment of the present invention; this non-dispersive infrared analyzer for determining the concentration of two components can to be advantageously used for determining the concentration of two components in the sample gas, one of which is of a low concentration and the other of which is of a high concentration. That is, the positive filter $F_1$, whose passband corresponds to infrared rays having the absorption bands of a low concentration component whose concentration is to be determined (for example, an optical bandpass filter which is permeable only to infrared rays having the absorption bands of CO), is inserted directly after (or before) one cell 2 having a greater length which is optimum for the determination of the concentration of a low concentration component and a positive filter $F_2$, whose passband corresponds to infrared rays having the absorption bands of a high concentration component whose concentration is to be determined (for example, an optical bandpass filter which is permeable only to infrared rays having the absorption bands of $CO_2$), is inserted directly after (or before) the other cell 2' having a smaller length which is optimum for the determination of the concentration of a high concentration component. Although it is desirable for the zero gas to be enclosed in the portion 2" of optical path formed by shortening the cell length of the cell 2' so that the determination of the concentration may not be influenced by components contained in the air, it is not essential for the construction of an analyzer in accordance with the present invention. Note that identical numerical designations in the drawing figures designate the same or similar constructive members of which repeated description have been omitted for brevity.

According to the above described construction, only infrared rays passing through the optical path A are incident upon the detector 7 while only infrared rays passing through the optical path B are incident upon the detector 8. The detector for determining the high concentration component as well as the detector for determining the low concentration component can provide an output having a good linearity, their S/N ratio is improved, and two components having a large difference in concentration therebetween can have their concentrations accurately determined since the lengths of the cells 2 and 2' can be selected so that they may be optimum for the determination of the concentration of each component. In addition, the mutual interference caused by the components whose concentration is to be determined and the interferences caused by components other than those components whose concentration to be determined can be prevented in the same manner as that of the above described preferred embodiment of FIG. 3.

FIG. 5 shows still another preferred embodiment of the present invention, characterized by the fact that the filter $F_2$, which is used with cell 2' of a smaller length, is omitted from the construction shown in FIG. 4. That is, in the case of the determination of the concentration of a low concentration component (for example, CO) it is necessary to increase the sensitivity of the detector since the absorption of infrared rays is small; thus, the determination is apt to be influenced by a high concentration component (for example, $CO_2$) contained in the sample gas and thus filter $F_1$ is indispensable. However, in the case of the determination of the concentration of a high concentration component (for example, $CO_2$) a sufficient accuracy of measurement can be attained in the practical application range even if the filter $F_2$ is omitted from the side of the cell 2' used for obtaining measuring signals for the high concentration component, since the absorption of infrared rays is large, and thus, the determination is not strongly influenced by the low concentration component whose concentration is to be determined and the other components in the sample gas. In addition, although optical band filters were inserted in the above described preferred embodiments, negative filters consisting of a gas filter also can be used. In these cases, for example, $CO_2$ gas and gases, which cause an undesirable influence upon the determination of the CO concentration, and are obviously contained in gases to be determined, are enclosed in filter $F_1$ as shown in FIGS. 3, 4, and 5. In addition, CO gas and gases, which cause an undesirable influence upon the determination of the $CO_2$ concentration, and are obviously contained in gases to be determined, are enclosed in filter $F_2$ as shown in FIGS. 3 and 4.

As obviously shown in the above described preferred embodiments, according to the present invention, two pneumatic detectors corresponding to the components whose concentration is to be determined are optically arranged in series with the light sources in order to determine the concentration of the two components in the sample gas, and thus, the determination is not significantly influenced by variations in the ambient temperature. Furthermore, a filter, which corresponds to absorption bands of at least one component of the components whose concentration is to be determined, is inserted directly before or after at least one cell, and thus, mutual interference caused by the components whose concentration is to be determined or interference caused by other components can be prevented and the S/N ratio can be improved.

We claim:

1. A non-dispersive infrared analyzer for determining the concentration of two components, wherein a zero fluid and a sample fluid are alternately supplied to two cells and wherein two pneumatic detectors are respectively optically arranged in series with two light sources, said two cells respectively sandwiched between said two light sources and said two detectors, said pneumatic detectors respectively providing outputs corresponding to the concentration of said components whose concentration is to be determined, said analyzer comprising at least one filter whose passband corresponds to absorption bands of one of said components whose concentration is to be determined, said filter being located directly adjacent to and optically in series with at least one of said two cells; wherein said two pneumatic detectors are each provided with two light receiving chambers corresponding to two independent light passages which are arranged in series optically.

2. An infrared analyzer as set forth in claim 1, wherein said two cells have the same length.

3. An infrared analyzer as set forth in claim 1, wherein said pneumatic detectors are condenser microphone type detectors.

4. An infrared analyzer as set forth in claim 1, wherein said pneumatic detectors are micro flow sensors.

5. An infrared analyzer as set forth in claim 1, wherein said filters are optical bandpass filters.

6. An infrared analyzer as set forth in claim 1, wherein said filters are gas filters.

7. A non-dispersive infrared analyzer for determining the concentration of two components, wherein a zero fluid and a sample fluid are alternately supplied to two cells and wherein two pneumatic detectors are respectively optically arranged in series with two light sources, said two cells respectively sandwiched between said two light sources and said two detectors, said pneumatic detectors respectively providing outputs corresponding to the concentration of said components whose concentration is to be determined, said analyzer comprising at least one filter whose passband corresponds to absorption bands of one of said components whose concentration is to be determined, said filter being located directly adjacent to and optically in series with at least one of said two cells, wherein said two cells have different lengths.

8. An infrared analyzer as set forth in claim 7, wherein one of said two cells has a relatively long length which is optimum for the determination of the concentration of a low concentration component of said components whose concentration is to be determined and the second of said two cells has a relatively short length which is optimum for the determination of the concentration of a high concentration component of said components whose concentration is to be determined.

* * * * *